(12) United States Patent
Loo et al.

(10) Patent No.: US 11,904,073 B2
(45) Date of Patent: Feb. 20, 2024

(54) BIOCOMPATIBLE ELECTROMECHANICAL CONNECTION FOR CERAMIC SUBSTRATE ELECTRONICS FOR BIOMEDICAL IMPLANT

(71) Applicant: Verily Life Sciences LLC, South San Francisco, CA (US)

(72) Inventors: Alexander Loo, Redwood City, CA (US); Damiano Patron, San Bruno, CA (US); Matthew Page, Florence, MA (US)

(73) Assignee: VERILY LIFE SCIENCES LLC, South San Francisco, CA (US)

(*) Notice: Subject to any disclaimer, the term of this patent is extended or adjusted under 35 U.S.C. 154(b) by 0 days.

(21) Appl. No.: 17/975,245

(22) Filed: Oct. 27, 2022

(65) Prior Publication Data

US 2023/0049960 A1    Feb. 16, 2023

Related U.S. Application Data

(63) Continuation of application No. 16/655,609, filed on Oct. 17, 2019, now Pat. No. 11,504,453.
(Continued)

(51) Int. Cl.
*A61N 1/02* (2006.01)
*A61N 1/05* (2006.01)
(Continued)

(52) U.S. Cl.
CPC ............ *A61L 31/026* (2013.01); *H01Q 1/273* (2013.01); *H01Q 23/00* (2013.01); *H01R 4/029* (2013.01);
(Continued)

(58) Field of Classification Search
CPC ... A61N 1/02; A61N 1/05; A61N 1/08; A61N 1/055139; A61N 1/372; A61N 1/375;
(Continued)

(56) References Cited

U.S. PATENT DOCUMENTS 5,333,095 A * 7/1994 Stevenson ............ A61N 1/3754
333/182
6,275,369 B1 * 8/2001 Stevenson ............ H03H 1/0007
361/309
(Continued)

OTHER PUBLICATIONS

Application No. EP19891163.8, Extended European Search Report, dated Aug. 10, 2022, 8 pages.
(Continued)

*Primary Examiner* — Xiaoliang Chen
(74) *Attorney, Agent, or Firm* — Kilpatrick Townsend & Stockton LLP

(57) ABSTRACT

A biocompatible electrical connection includes a substrate; a ferrule having a concentric flange at a first end of the ferrule; a first adhesive; and a second adhesive. The first adhesive adheres a first surface of the concentric flange of the ferrule to a surface of the substrate. The second adhesive fills an annular space between a hole in the substrate and the ferrule. The first adhesive or the second adhesive forms a conductive path on the surface of the substrate between the ferrule and a circuit pattern on the substrate.

12 Claims, 10 Drawing Sheets

Related U.S. Application Data

(60) Provisional application No. 62/772,942, filed on Nov. 29, 2018.

(51) Int. Cl.

| | | |
|---|---|---|
| *A61N 1/08* | (2006.01) | |
| *A61N 1/372* | (2006.01) | |
| *A61N 1/375* | (2006.01) | |
| *H05K 1/02* | (2006.01) | |
| *H05K 1/18* | (2006.01) | |
| *H05K 3/00* | (2006.01) | |
| *H01G 4/005* | (2006.01) | |
| *H01G 4/018* | (2006.01) | |
| *H01G 4/12* | (2006.01) | |
| *H01G 4/30* | (2006.01) | |
| *H01G 4/35* | (2006.01) | |
| *H01G 4/40* | (2006.01) | |
| *H01G 4/224* | (2006.01) | |
| *H01G 4/228* | (2006.01) | |
| *H01G 4/236* | (2006.01) | |
| *A61L 31/02* | (2006.01) | |
| *H01R 4/02* | (2006.01) | |
| *H01R 4/60* | (2006.01) | |
| *H01R 43/02* | (2006.01) | |
| *H05K 3/32* | (2006.01) | |
| *H01R 4/04* | (2006.01) | |
| *H01Q 1/27* | (2006.01) | |
| *H01Q 23/00* | (2006.01) | |
| *H01R 12/53* | (2011.01) | |

(52) U.S. Cl.
CPC .............. *H01R 4/04* (2013.01); *H01R 4/60* (2013.01); *H01R 12/53* (2013.01); *H01R 43/0256* (2013.01); *H05K 1/18* (2013.01); *H05K 3/0047* (2013.01); *H05K 3/321* (2013.01); *H05K 3/328* (2013.01); *H05K 2201/10257* (2013.01); *H05K 2201/10295* (2013.01); *H05K 2203/049* (2013.01)

(58) Field of Classification Search
CPC .. A61N 1/3605; A61N 1/3754; A61N 1/3756; A61N 1/3787; H05K 1/095; H05K 1/18; H05K 1/115; H05K 1/181; H05K 3/00; H05K 3/0047; H05K 3/47; H05K 3/321; H05K 3/328; H05K 3/4038; H05K 1/02; H01Q 1/007; H01Q 1/243; H01Q 1/248; H01Q 1/273; H01Q 1/2283; H01G 4/005; H01G 4/018; H01G 4/12; H01G 4/30; H01G 4/35; H01G 4/40; H01G 4/224; H01G 4/228; H01G 4/236

USPC ...... 128/899; 361/118, 271, 302, 303, 306.1, 361/309, 509, 519, 521; 174/50.6, 126.2, 174/650, 152 G; 429/163, 175; 607/5, 607/37, 116

See application file for complete search history.

(56) References Cited

U.S. PATENT DOCUMENTS

| | | |
|---|---|---|
| 7,575,829 B1 | 8/2009 | Nakahara et al. |
| 9,492,659 B2 | 11/2016 | Tang et al. |
| 10,449,375 B2 | 10/2019 | Frustaci et al. |
| 2001/0050837 A1* | 12/2001 | Stevenson ............... H01G 4/35 29/25.42 |
| 2004/0201947 A1* | 10/2004 | Stevenson ............ A61N 1/3752 361/302 |
| 2005/0247475 A1 | 11/2005 | Stevenson et al. |
| 2006/0085043 A1 | 4/2006 | Stevenson |
| 2006/0175071 A1* | 8/2006 | Knappen ................ H01G 4/35 174/50.56 |
| 2007/0053137 A1 | 3/2007 | Fu et al. |
| 2007/0217121 A1 | 9/2007 | Fu et al. |
| 2009/0116167 A1* | 5/2009 | Stevenson .......... H01R 13/7195 338/322 |
| 2009/0259265 A1* | 10/2009 | Stevenson .......... A61N 1/37512 607/2 |
| 2009/0288280 A1 | 11/2009 | Brendel et al. |
| 2011/0255260 A1* | 10/2011 | Weber ...................... H05K 7/14 200/341 |
| 2012/0176279 A1* | 7/2012 | Merz ....................... H01Q 1/48 343/702 |
| 2013/0060312 A1 | 3/2013 | Tyer et al. |
| 2013/0070387 A1 | 3/2013 | Stevenson et al. |
| 2013/0100595 A1* | 4/2013 | Koester .................... H01L 25/16 361/679.01 |
| 2013/0138187 A1 | 5/2013 | Iyer et al. |
| 2013/0184797 A1* | 7/2013 | Tang ....................... A61N 1/08 607/116 |
| 2014/0163646 A1* | 6/2014 | Tischendorf .......... A61N 1/0551 607/116 |
| 2014/0168850 A1* | 6/2014 | Stevenson ............ A61N 1/3718 361/302 |
| 2015/0314131 A1 | 11/2015 | Stevenson et al. |
| 2016/0106988 A1* | 4/2016 | Koester ................ H01L 23/055 29/896.21 |
| 2016/0263384 A1* | 9/2016 | Stevenson ............... H01G 4/12 |
| 2017/0281957 A1 | 10/2017 | Howard |
| 2017/0338043 A1* | 11/2017 | Das ........................ H01G 9/10 |
| 2018/0085591 A1 | 3/2018 | Li et al. |
| 2018/0126175 A1* | 5/2018 | Seitz ...................... H01G 4/018 |
| 2018/0126176 A1* | 5/2018 | Seitz ..................... H01B 17/303 |
| 2018/0169417 A1* | 6/2018 | Urbanski ............. H05K 5/0095 |
| 2018/0178016 A1* | 6/2018 | Frustaci ................. A61N 1/08 |
| 2018/0197661 A1* | 7/2018 | Seitz ..................... C04B 41/5194 |
| 2018/0304084 A1* | 10/2018 | Stevenson ............. H01R 4/022 |
| 2018/0361164 A1* | 12/2018 | Stevenson ............ A61N 1/3754 |

OTHER PUBLICATIONS

Application No. PCT/US2019/056718 , International Search Report and Written Opinion, dated Jan. 10, 2020, 9 pages.

\* cited by examiner

BIOCOMPATIBLE ELECTROMECHANICAL CONNECTION FOR CERAMIC SUBSTRATE ELECTRONICS FOR BIOMEDICAL IMPLANT

CROSS-REFERENCE TO RELATED APPLICATION

The present application is a continuation of U.S. patent application Ser. No. 16/655,609 filed Oct. 17, 2019, which claims the benefit of priority to U.S. Provisional Application No. 62/772,942, filed Nov. 29, 2018, the entire contents of both of which are hereby incorporated by reference herein for all purposes.

BACKGROUND

Unless otherwise indicated herein, the materials described in this section are not prior art to the claims in this application and are not admitted to being prior art by inclusion in this section.

Implantable devices require the use of biocompatible materials. In some cases, the implantable devices may communicate with external equipment. In order to communicate with the external equipment, an implantable device may include an antenna. The antenna may connect to the electronics of the implantable device using vias to form the electrical connection with the associated electronics. However, because of the required use of biocompatible materials for the vias, drilling the vias to accept wire leads presents difficulty due to the toughness of the via material. In addition, because biocompatible soldering materials are not available, welding must be used to form electrical connections at the vias. However, the welding operation can cause ablation of the via material resulting in a poor or no electrical connection being formed as well as generating carbonized soot that adversely affects cleanliness of the device.

A methodology to ensure a good welded joint between the vias and the wire leads while maintaining overall biocompatibility is needed.

SUMMARY

Apparatuses and methods for a biocompatible electrical connection are provided.

According to various aspects there is provided a biocompatible electrical connection. In some aspects, the biocompatible electrical connection may include a substrate; a ferrule having a concentric flange at a first end of the ferrule; a first adhesive; and a second adhesive. The first adhesive adheres a first surface of the concentric flange of the ferrule to a surface of the substrate. The second adhesive fills an annular space between a hole in the substrate and the ferrule. The first adhesive or the second adhesive forms a conductive path on the surface of the substrate between the ferrule and a circuit pattern on the substrate.

According to various aspects there is provided a method for forming a biocompatible electrical connection. In some aspects, the method may include applying a first adhesive on a surface of a substrate around a circumference of a hole in the substrate; inserting a ferrule comprising a concentric flange at a first end into the hole. The first adhesive adheres a first surface of the concentric flange to the surface of the substrate. The method may further include filling an annular space between the hole and the ferrule with a second adhesive; and forming a conductive path between the ferrule and a circuit pattern on the surface of the substrate using the first adhesive or the second adhesive.

According to various aspects there is provided a biocompatible device. In some aspects, the biocompatible device may include electronic circuitry enclosed in a conductive biocompatible housing; a biocompatible antenna disposed external to the conductive biocompatible housing and electrically connected to the electronic circuitry; and a biocompatible electrical connector configured to electrically connect the biocompatible antenna to the electronic circuitry. The biocompatible electrical connector includes a ferrule having a concentric flange at a first end of the ferrule; a first adhesive; a second adhesive; and a substrate. The first adhesive adheres a first surface of the concentric flange of the ferrule to a surface of the substrate, the second adhesive fills an annular space between a hole in the substrate and the ferrule, and the first adhesive or the second adhesive forms a conductive path on the surface of the substrate between the ferrule and a circuit pattern on the substrate.

Numerous benefits are achieved by way of the various embodiments over conventional techniques. For example, the various embodiments provide methods and systems that can be used to provide biocompatible electrical connections to components disposed outside of a hermetic enclosure. In some embodiments, an implantable device may receive communication signals through an external antenna connected using biocompatible vias to a hermetically sealed electronics package. These and other embodiments along with many of its advantages and features are described in more detail in conjunction with the text below and attached figures.

BRIEF DESCRIPTION OF THE DRAWINGS

Aspects and features of the various embodiments will be more apparent by describing examples with reference to the accompanying drawings, in which.

DETAILED DESCRIPTION

Figure 1:
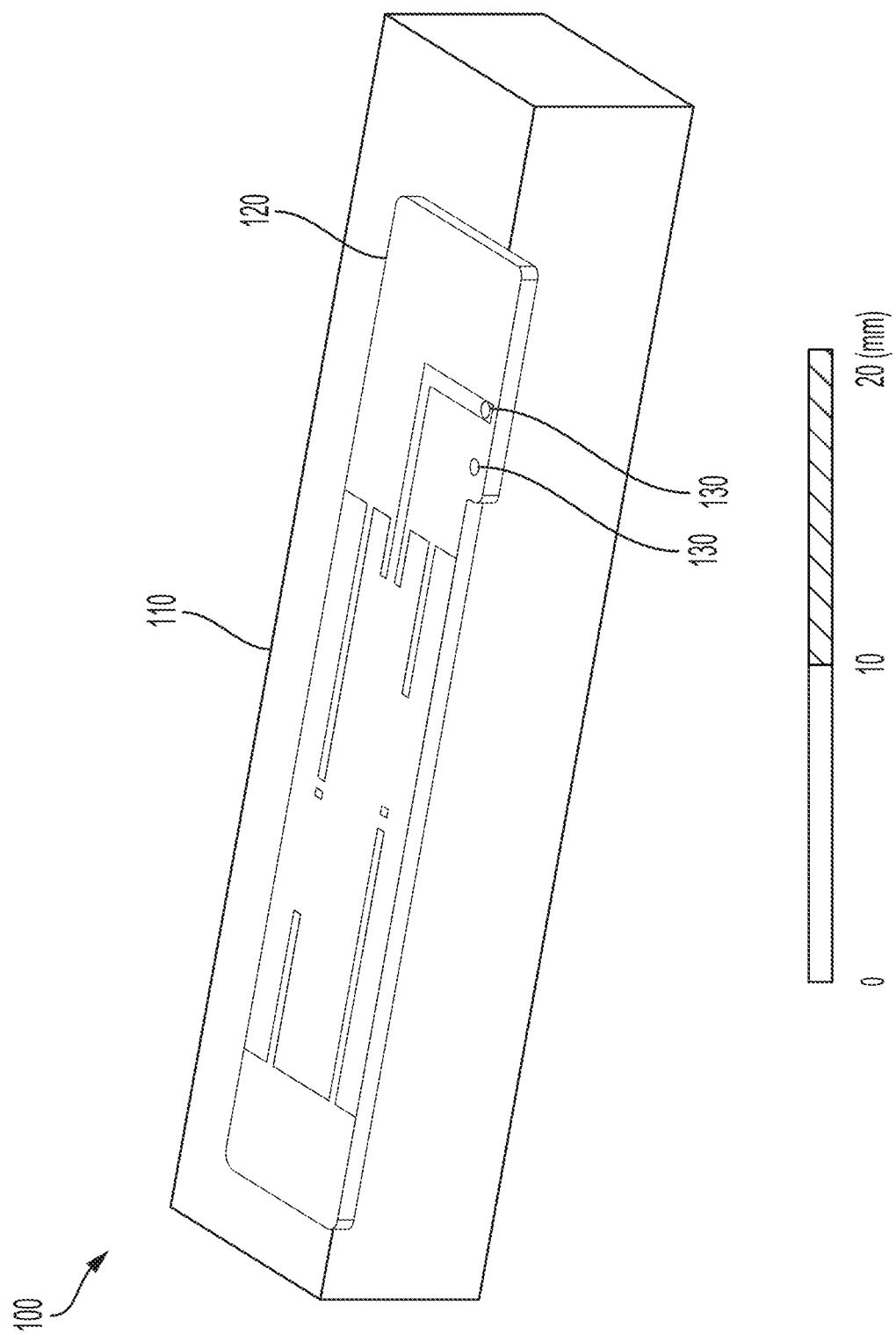
FIG. 1 is a diagram illustrating a representative implantable device having a PCB antenna according to various aspects of the present disclosure.

While certain embodiments are described, these embodiments are presented by way of example only, and are not intended to limit the scope of protection. The apparatuses, methods, and systems described herein may be embodied in a variety of other forms. Furthermore, various omissions, substitutions, and changes in the form of the example methods and systems described herein may be made without departing from the scope of protection.

An implantable device may use a biocompatible printed circuit board (PCB) antenna for communications (e.g., Bluetooth® Low Energy (BLE) communications) with external equipment. The PCB antenna may include a ceramic substrate with gold/platinum traces and gold/platinum vias or ceramic/gold/platinum vias. The antenna traces may electrically connected to the vias with a gold/platinum ink or other biocompatible conductive material. While example embodiments are described using a ceramic substrate, embodiments are not limited to this implementation. In other embodiments the substrate may be any biocompatible material that permits drilling of vias and printing biocompatible conductive materials, for example, but not limited to, gold or other biocompatible conductive materials, to form an antenna. The PCB antenna may be connected to an electronics package of the implantable device by wire leads inserted through vias in the PCB antenna and the wire leads welded to the vias.

In accordance with various aspects of the present disclosure, techniques related to forming vias through a ceramic PCB substrate to connect an antenna to electronic circuitry are provided. The vias may include an outer layer of ceramic, gold, or platinum and a platinum-iridium (Pt—Ir) ferrule. In some embodiments, the ferrule may be a gold or implant grade stainless steel, for example, but not limited to, MP35 or MP35N stainless steel, ferrule. Laser welding may be performed to secure a lead (e.g., a Pt—Ir wire lead) within the via to electrically connect the antenna to the electronic circuitry. More specifically, a hole for the via may be formed in the ceramic substrate. A platinum-iridium (Pt—Ir) or implant grade stainless steel ferrule may be inserted into the hole. One of ordinary skill in the art will appreciate that other electrically conductive metals that are biocompatible and suitable for long term implants may be used without departing from the scope of the present disclosure. The internal diameter of the ferrule may be sized for optimal welding of a lead inserted into the ferrule. The diameter of the hole in the ceramic substrate may be sized to provide a nominal gap between the outer diameter of the ferrule and the hole in the ceramic substrate. The gap may then be filled in with a gold/platinum material, for example, but not limited to, a gold/platinum ink, a ceramic/gold/platinum ink, or other material, to mechanically and electrically join the ferrule to the ceramic substrate. The entire assembly may then be fired to bond all items together. The assembly may later be integrated with an electronics assembly with wire leads inserted into the vias and welded in place without the need to drill out the vias. The additional thermal mass of the assembly at least in part enables successful welding of the wire leads to the vias.

FIG. 1 is a diagram illustrating a representative implantable device 100 having a PCB antenna 120 in accordance with various aspects of the present disclosure. The implantable device 100 may be a miniature device. For example, the implantable device 100 may less than one hundred millimeters along its longest dimension. One of ordinary skill in the art will appreciate that that this dimension is merely exemplary and that an implantable device may have larger or smaller dimensions without departing from the scope of the present disclosure.

Referring to FIG. 1, the implantable device 100 may include a hermetic enclosure 110 and a PCB antenna 120. The hermetic enclosure 110 may house an electronics package including components (e.g., integrated circuits, PCBs, passive components, etc.) for performing the designed functions of the implantable device. The hermetic enclosure 110 may be formed from a conductive biocompatible material, for example, titanium or another conductive biocompatible material, and may provide electromagnetic shielding to protect the electronics package housed within the hermetic enclosure 110 from electromagnetic interference.

The PCB antenna 120 may include a ceramic substrate printed with electrically conductive traces. The PCB antenna 120 may also include vias 130 configured to connect to the PCB antenna 120 to the electronics package enclosed by the hermetic enclosure 110. The antenna may be encapsulated with biocompatible epoxy after assembly. The PCB antenna 120 may enable communication, for example, BLE communications or communications using other communication protocols, between the electronics package and external equipment.

Figure 2A:
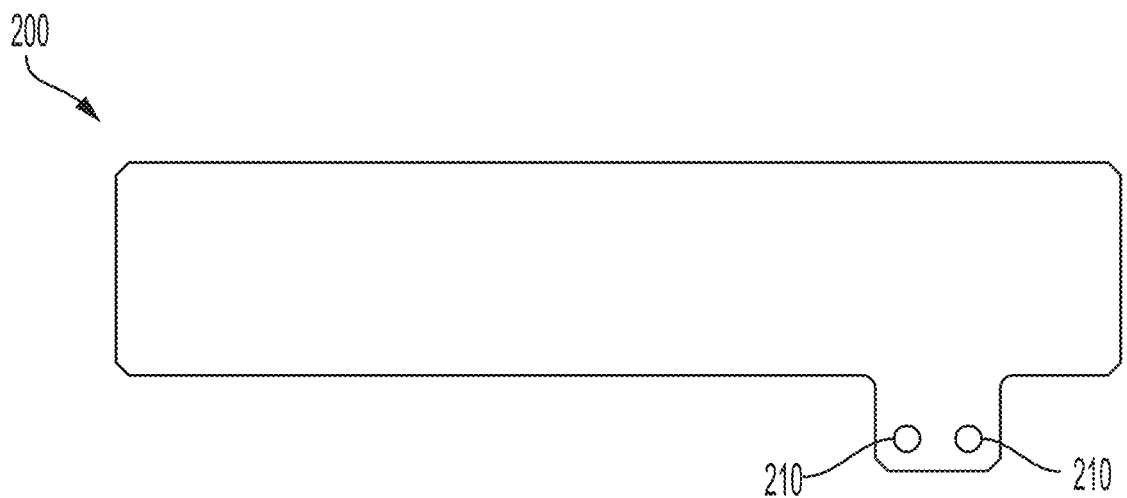
FIGS. 2A and 2B are a top view and a side view, respectively, of an exemplary ceramic substrate according to various aspects of the present disclosure.
Figure 2B:
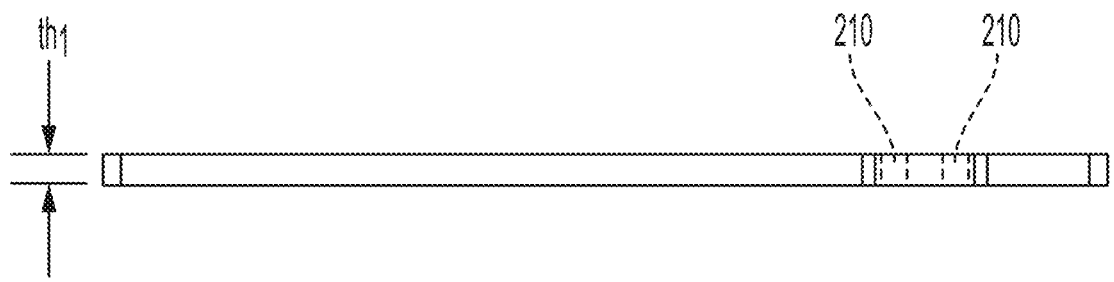

FIGS. 2A and 2B are a top view and a side view, respectively, of an exemplary ceramic substrate 200 for a PCB antenna in accordance with various aspects of the present disclosure. Referring to FIGS. 2A and 2B, the ceramic substrate 200 may be fabricated from a ceramic material, for example, but not limited to, alumina or another ceramic material. The ceramic substrate 200 may have a thickness $th_1$ of approximately 0.6 mm (0.024 inches).

A plurality of holes 210 may be formed in the ceramic substrate 200 to accommodate vias. For example, the plurality of holes 210 may be formed by drilling the ceramic substrate 200 using an appropriately sized drill bit. In some embodiments, drilling may be performed by laser drilling, water jet drilling, or other suitable drilling technology. Each of the plurality of holes 210 may have a diameter of approximately 0.84 mm (0.033 inches). One of ordinary skill in the art will appreciate that the hole diameter may vary without departing from the scope of the present disclosure. In accordance with various aspects of the present disclosure, the diameter of each of the plurality of holes 210 may be smaller than an expected outside diameter of a ferrule that will be inserted in the hole 210 and the hole 210 may be match drilled using an appropriately sized drill bit to enlarge the hole 210 to provide a specified annular space between the hole 210 and the ferrule. An antenna pattern (not shown) may be printed on the ceramic substrate 200 using a suitable process, for example, screen printing or another process.

Figure 3:
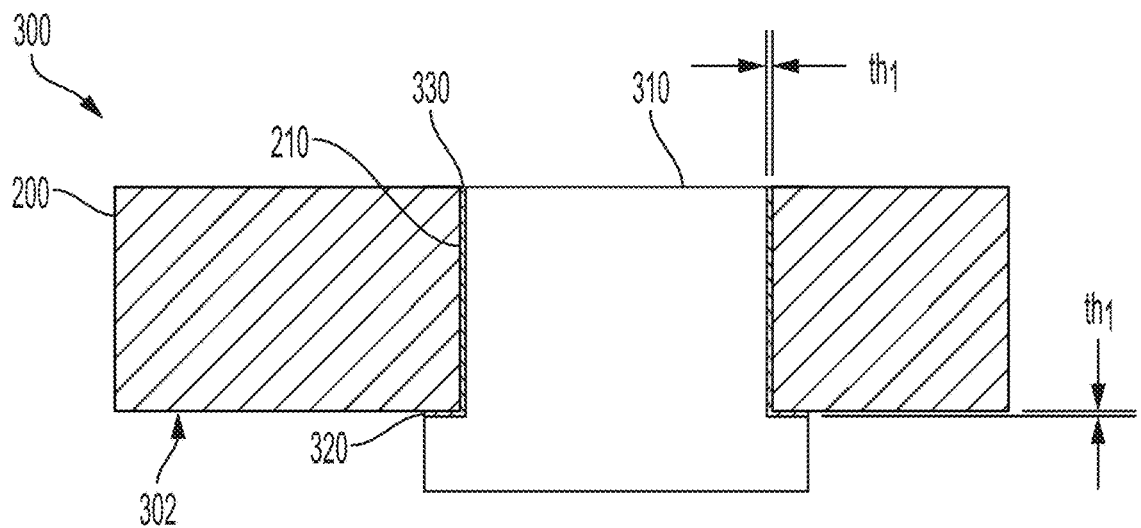
FIG. 3 is a cross-sectional view of a via of a ceramic substrate according to various aspects of the present disclosure.
Figure 4:
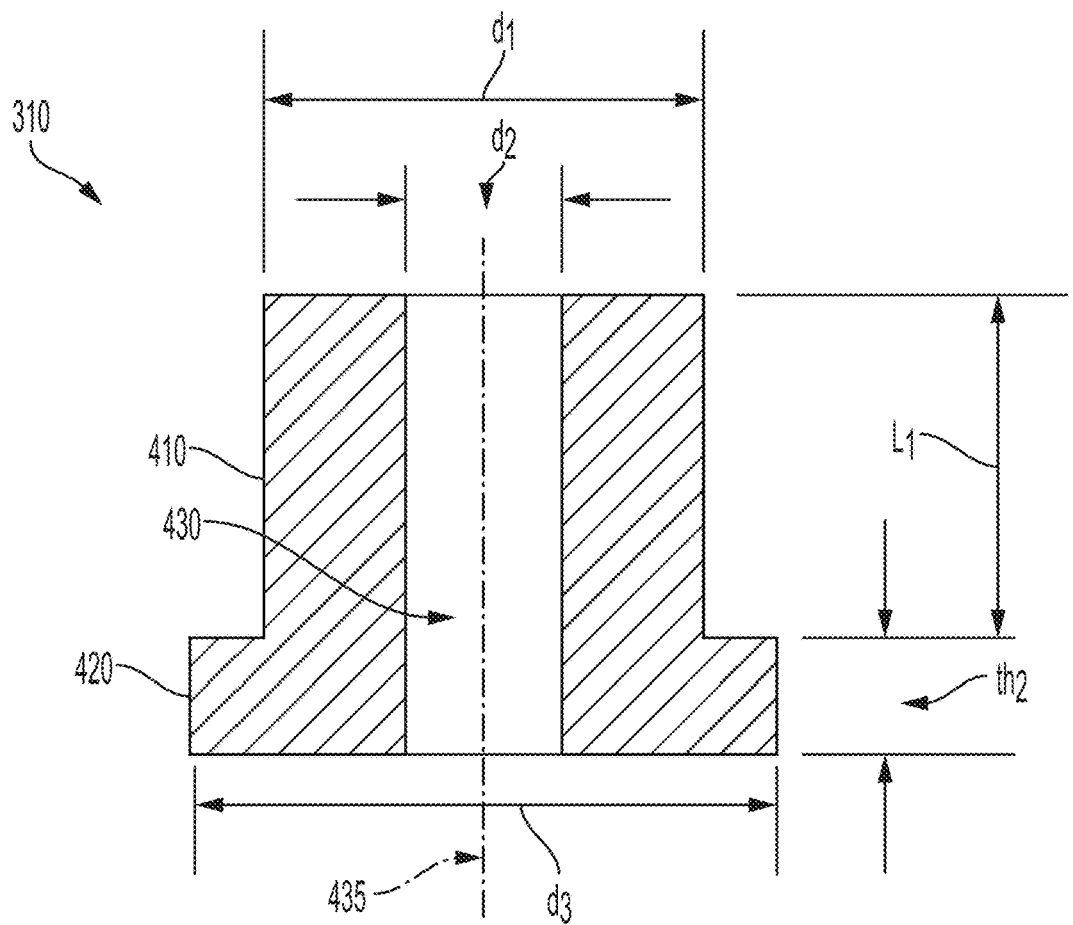
FIG. 4 is a cross-sectional view of a ferrule according to various aspects of the present disclosure.

FIG. 3 is a cross-sectional view of a via 300 of a ceramic substrate 200 in accordance with various aspects of the present disclosure. Referring to FIG. 3, the via 300 may include a ferrule 310 inserted into a hole (e.g., the hole 210) in the ceramic substrate 200, a first adhesive 320, and a second adhesive 330. FIG. 4 is a cross-sectional view of a ferrule 310 in accordance with various aspects of the present disclosure.

Referring to FIG. 4, the ferrule 310 may include a main body 410, a flange 420, and a through hole 430. The ferrule 310 may be substantially cylindrical. The main body 410 of the ferrule 310 may have an outside diameter (OD) $d_1$ of approximately 0.79 mm (0.031 inches). The length $L_1$ of the main body 410 may be approximately 0.6 mm (0.024 inches) and/or may be commensurate with a thickness of the ceramic substrate 200. The flange 420 of the ferrule 310 may have an OD $d_3$ of approximately 0.79 mm (0.031 inches) and may overlap the ceramic substrate 200 around the circumference of the hole (e.g., the hole 210) in the ceramic substrate 200 into which the ferrule 310 is inserted. The flange 420 may have a thickness $th_2$ of approximately 0.20 mm (0.008 inches). The through hole 430 of the ferrule 310 may be substantially cylindrical and may be formed substantially along the centerline 435 of the ferrule 310. The through hole 430 may have a diameter of approximately 0.28 mm (0.0.11 inches). The ferrule 310 may be formed from a Pt—Ir material having a composition of, for example, 90% Pt and 10% Ir or another percentage composition, or implant grade stainless steel, for example, but not limited to, MP35 or MP35N stainless steel. One of ordinary skill in the art will appreciate that other electrically conductive metals that are biocompatible and suitable for long term implants may be used without departing from the scope of the present disclosure.

One of ordinary skill in the art will appreciate that the dimensions of the ferrule 310 are presented for ease of explanation and that the dimensions are exemplary and may vary without departing from the scope of the present disclosure. In particular, the OD $d_1$ of the of the main body 410 of the ferrule 310 may vary based on material and manufacturing tolerances. In some embodiments, the ferrule and/or the through hole of the ferrule may be formed in other shapes, for example, but not limited to, pentagonal, hexagonal, etc. One of ordinary skill in the art will appreciate that these configuration as well as variations of the disclosed configurations may be used without departing from the scope of the present disclosure.

Referring again to FIG. 3, the plurality of holes 210 may be match drilled to the OD $d_1$ of the of the main body 410 of the as-machined ferrules 310. For example, for each lot of ferrules 310, the OD $d_1$ of the of the main body 410 of the as-machined ferrules 310 may be measured and a representative statistic, for example, but not limited to, an average OD may be determined. A drill bit size may be selected to drill or enlarge the plurality of holes 210 in the ceramic substrate 200 based on the representative statistic.

In accordance with various aspects of the present disclosure, a drill bit size may be selected to drill or enlarge the plurality of holes 210 such that an annular space of approximately 0.03 mm (0.001 inches) between the OD $d_1$ of the of the main body 410 of the as-machined ferrules 310 and the plurality of holes 210 in the ceramic substrate 200 is provided. In other words, the drill bit size may be selected to drill or enlarge the plurality of holes 210 in the ceramic substrate 200 such that each of the plurality of holes 210 has a diameter approximately 0.06 mm (0.002 inch) larger than the OD $d_1$ of the of the main body 410 of the ferrule 310. In some embodiments, drilling may be performed by laser drilling, water jet drilling, or other suitable drilling technology.

The first adhesive 320 may be a platinum-gold (Pt—Au) ink, a ceramic-platinum-gold (ceramic-Pt—Au) ink, or another adhesive. The first adhesive 320 may be applied to a first surface 302 of the ceramic substrate 200 around a circumference of each of the plurality of holes 210 prior to insertion of the ferrule 310 into the hole (e.g., the hole 210) in the ceramic substrate 200. For example, the first adhesive 320 may be applied using a screen printing process or another suitable process for applying the first adhesive 320. The first adhesive 320 may serve to adhere the flange 420 of the ferrule 310 to the ceramic substrate 200, thereby also providing a seal when the annular space between the main body 410 of the ferrule 310 and the hole 210 is filled with the second adhesive 330. The second adhesive 330 may be a platinum-gold (Pt—Au) ink, a ceramic-platinum-gold (ceramic-Pt—Au) ink, or another adhesive. The first adhesive 320 and the second adhesive 330 may be the same or different adhesive. One of ordinary skill in the art will appreciate that other electrically conductive, biocompatible adhesives capable of withstanding the firing processes that are compatible with the substrate and ferrule materials, and having some moderate structural capabilities may be used without departing from the scope of the present disclosure.

After the ferrule 310 is inserted into the hole (e.g., the hole 210) in the ceramic substrate 200, the remaining annular space between the ferrule 310 and the hole 210 in the ceramic substrate 200 may be filled with the second adhesive 330. For example, the second adhesive 330 may be injected into the annular space using a syringe or the annular space may be filled with the second adhesive 330 by another method. Since the plurality of holes 210 is match-drilled to the OD $d_1$ of the of the main body 410 of the as-machined ferrules 310, a consistent thickness of the second adhesive 330 that bonds the ferrule 310 inside the hole 210 may be maintained. The assembly including the ceramic substrate 200, the ferrule 310, the first adhesive 320, and the second adhesive 330 may be fired together to cure the adhesives and form the bond between the ceramic substrate 200 and the ferrule 310. In some embodiments the ceramic substrate 200, the ferrule 310, and the first adhesive 320 may be fired to cure the first adhesive 320. The second adhesive 330 may be applied and the assembly fired again to cure the second adhesive 330.

Figure 5A:
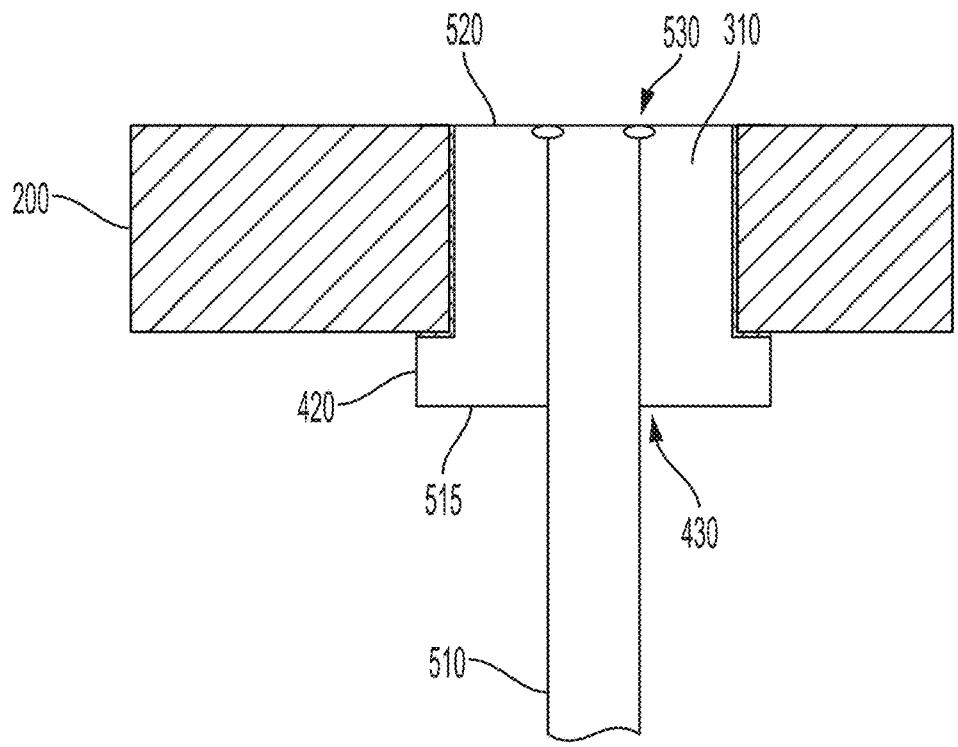
FIGS. 5A and 5B are cross-sectional views illustrating a wire lead inserted in a ferrule in accordance with various aspects of the present disclosure.
Figure 5B:
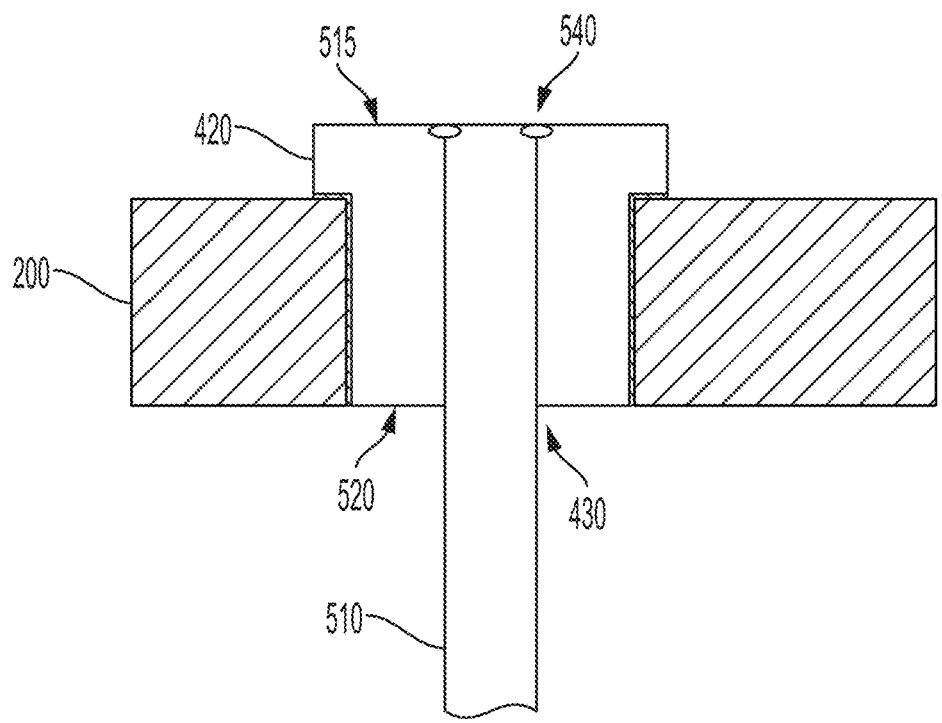

FIGS. 5A and 5B are cross-sectional views illustrating a wire lead inserted in a ferrule in accordance with various aspects of the present disclosure. The ceramic substrate 200 with one or more vias may be integrated with an electronics assembly by inserting wire leads into the vias and welding the wire leads in place. Referring to FIG. 5A, a wire lead 510 may be inserted into the through hole 430 of the ferrule 310 in a direction from a first surface 515 (i.e., the flange 420 surface) to a second surface 520. The wire lead 510 may be a Pt—Ir wire lead or a metal lead having another composition. The wire lead 510 may have a slip fit with the diameter of the through hole 430.

The end of the wire lead 510 inserted into the through hole 430 of the ferrule 310 may be positioned approximately even with the second surface 520 of the ferrule 310. In some embodiments, the wire lead 510 may be pre-trimmed to an appropriate length to be positioned approximately even with the second surface 520 of the ferrule 310. In some embodiments, the wire lead 510 may be pre-trimmed to a length extending past the second surface 520 of the ferrule 310 and then trimmed to an appropriate length to be positioned approximately even with the second surface 520 of the ferrule 310 taking care to avoid forming a peak on the end of the wire lead. A weld joint 530 may be formed around the circumference of the through hole 430 between the end of the wire lead 510 inserted into the ferrule 310 and the second surface 520 of the ferrule 310. The weld joint 530 may be formed by laser welding or another suitable welding technology, for example, but not limited to, resistance welding. The welded joint 530 may form a biocompatible mechanical and electrical connection.

FIG. 5B illustrates a connection between the wire lead 510 and the ferrule 310 with the wire lead 510 inserted into the ferrule 310 from the opposite direction as compared to FIG. 5A. Referring to FIG. 5B, a wire lead 510 may be inserted into the through hole 430 of the ferrule 310 in a direction from a second surface 520 to a first surface 515 (i.e., the flange 420 surface). The wire lead 510 may be a Pt—Ir wire lead or a metal lead having another composition. The wire lead 510 may have a slip fit with the diameter of the through hole 430. The end of the wire lead 510 inserted into the through hole 430 of the ferrule 310 may be positioned approximately even with the first surface 515 of the ferrule 310. A weld joint 540 may be formed around the circumference of the through hole 430 between the end of the wire lead 510 inserted into the ferrule 310 and the first surface 515 of the ferrule 310. The weld joint 540 may be formed by laser welding or another suitable welding technology, for example, but not limited to, resistance welding. The welded joint 540 may form a biocompatible mechanical and electrical connection.

Figure 6:
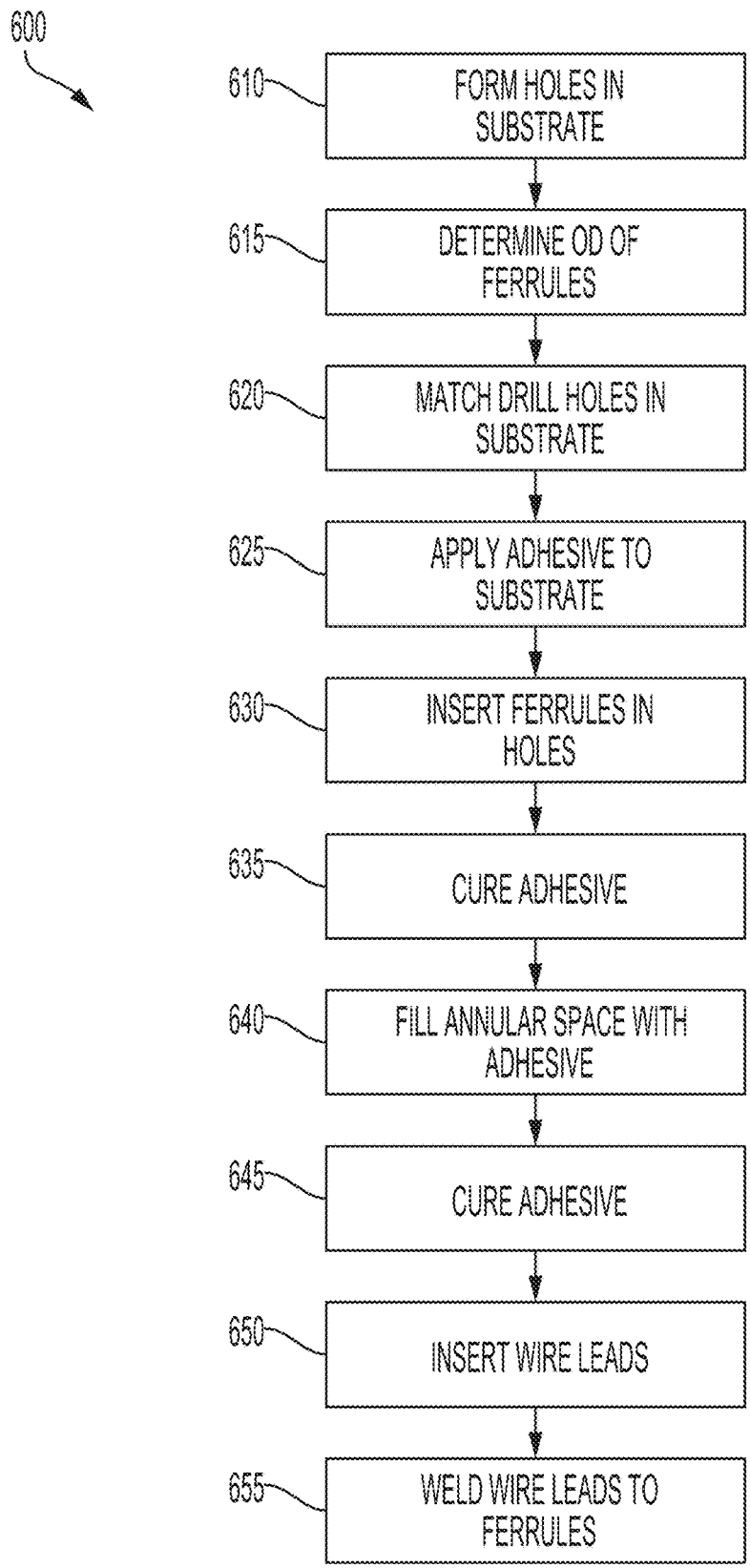
FIG. 6 is a flowchart of a method of forming a via in accordance with various aspects of the present disclosure.

FIG. 6 is a flowchart of a method 600 of forming a via in accordance with various aspects of the present disclosure. Referring to FIG. 6, at block 610 a plurality of holes may be formed in a substrate, for example, but not limited to, a ceramic substrate. The diameter of each of the plurality of holes may be smaller than an expected outside diameter of a ferrule that will be inserted in the hole. Alternatively, in some embodiments, the substrate may not yet include holes. At block 615, the outside diameter (OD) of the ferrules to be inserted in the holds may be determined. For example, for each lot of ferrules 310, the OD $d_1$ of the of the main body 410 of the as-machined ferrules 310 may be measured and a representative statistic, for example, but not limited to, an average OD determined.

At block 620, the holes in the substrate may be match drilled to the average OD of the ferrules 310. For example, a drill bit size may be selected to drill or enlarge the plurality of holes 210 in the ceramic substrate 200 based on the representative statistic (e.g., the average OD) determined for the as-machined ferrules 310. The drill bit size may be selected to drill or enlarge the plurality of holes to provide an annular space of approximately 0.03 mm (0.001 inches) between the OD $d_1$ of the of the main body 410 of the as-machined ferrules 310 and the plurality of holes 210 in the ceramic substrate 200. In other words, the drill bit size may be selected to drill or enlarge the plurality of holes 210 in the ceramic substrate 200 such that each hole 210 has a diameter approximately 0.06 mm (0.002 inch) larger than the OD $d_1$ of the of the main body 410 of the ferrule 310. In some embodiments, drilling may be performed by laser drilling, water jet drilling, or other suitable drilling technology.

At block 625 a first adhesive may be applied to the substrate. The first adhesive may be a platinum-gold (Pt—Au) ink, a ceramic-platinum-gold (ceramic-Pt—Au) ink, or another adhesive. The first adhesive may be applied to a first surface 302 of the ceramic substrate 200 around a circumference of each of the plurality of holes 210 prior to insertion of the ferrule 310 into the hole. For example, the first adhesive may be applied using a screen printing process or another suitable process for applying the first adhesive. The first adhesive may serve to adhere the flange 420 of the ferrule 310 to the ceramic substrate 200. At block 630, the ferrule 310 may be inserted into the hole 210 and may adhere to the substrate by the first adhesive. At block 635, the ceramic substrate 200, the ferrule 310, and the first adhesive 320 may be fired to cure the first adhesive 320.

At block 640, the annular space between the ferrule 310 and the hole in the ceramic substrate may be filled with a second adhesive. For example, the second adhesive may be injected into the annular space using a syringe or the annular space may be filled with the second adhesive by another method. Since the plurality of holes 210 is match-drilled to the OD $d_1$ of the of the main body 410 of the as-machined ferrules 310, a consistent thickness of the second adhesive that bonds the ferrule 310 inside hole 210 may be maintained. At block 645, the adhesive may be cured. The assembly including the ceramic substrate 200, the ferrule 310, the first adhesive, and the second adhesive may be fired together to cure the second adhesive and complete the bond between the ceramic substrate 200 and the ferrule 310. In some embodiments the curing operation at block 635 may be omitted and the ceramic substrate 200, the ferrule 310, the first adhesive and the second adhesive may be fired together to cure the first adhesive and the second adhesive.

At block 650, a wire lead may be inserted into each ferrule. The wire lead 510 may be a Pt—Ir wire lead or a metal lead having another composition. The wire lead 510 may have a slip fit with the diameter of the through hole 430. The wire lead 510 may be inserted into the through hole 430 of the ferrule 310 in a direction from a first surface 515 (i.e., the flange 420 surface) to a second surface 520. The end of the wire lead 510 inserted into the through hole 430 of the ferrule 310 may be positioned approximately even with the second surface 520 of the ferrule 310. Alternatively, the wire lead 510 may be inserted into the through hole 430 of the ferrule 310 in a direction from a second surface 520 to a first surface 515 (i.e., the flange 420 surface). The end of the wire lead 510 inserted into the through hole 430 of the ferrule 310 may be positioned approximately even with the first surface 515 of the ferrule 310.

At block 655, the wire lead may be welded to the ferrule. A weld joint may be formed around the circumference of the through hole 430 between the end of the wire lead 510 inserted into the ferrule 310 and the surface of the ferrule 310. The weld joint may be formed by laser welding or another suitable welding technology, for example, but not limited to, resistance welding. The welded joint may form a biocompatible mechanical and electrical connection.

It should be appreciated that the specific steps illustrated in FIG. 6 provide a particular method of forming a via according to another embodiment of the present invention. Other sequences of steps may also be performed according to alternative embodiments. For example, alternative embodiments of the present invention may perform the steps outlined above in a different order. Moreover, the individual steps illustrated in FIG. 6 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 7A:
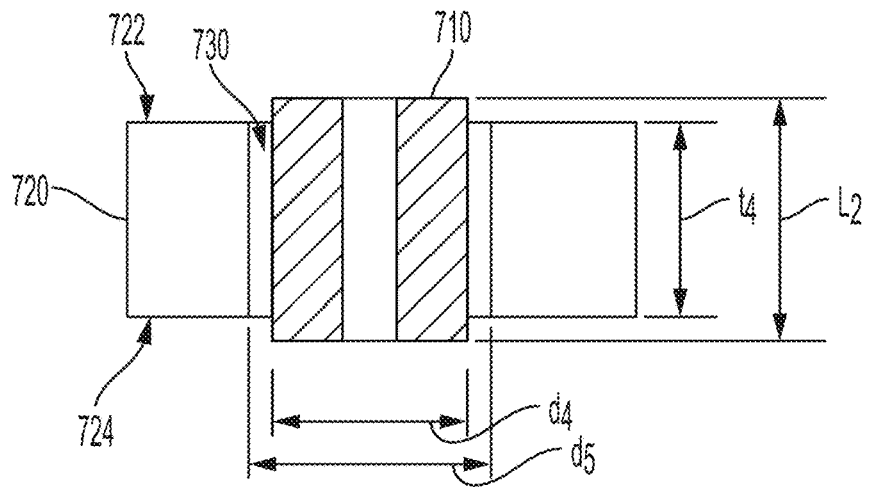
FIGS. 7A and 7B are cross-sectional views illustrate a via formed with a ferrule without a flange in accordance with various aspects of the present disclosure.
Figure 7B:
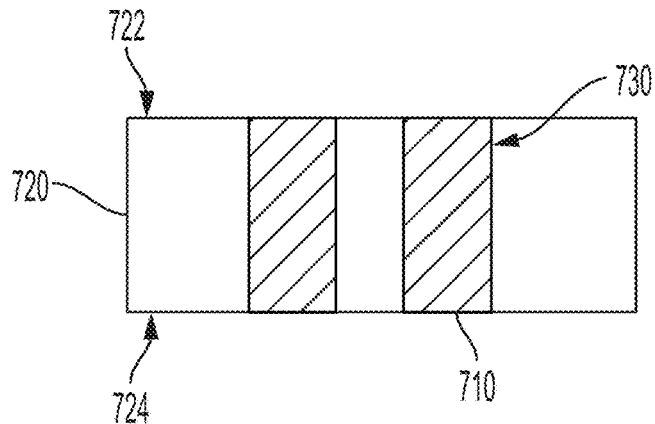

While the above embodiments are describe including a ferrule having a flange, embodiments in accordance with the present disclosure are not limited to those implementations. In some embodiments, vias may be formed in a ceramic substrate using ferrules without a flange (i.e., the flange 420). FIGS. 7A and 7B are cross-sectional views illustrating a via formed with a ferrule without a flange in accordance with various aspects of the present disclosure.

Referring to FIG. 7A, a ferrule 710 may have a length $L_2$ greater than a thickness $t_4$ of a substrate 720 (e.g., a ceramic substrate or other substrate), and an outside diameter (OD) $d_4$ less than a diameter $d_5$ of a hole 730 formed in the substrate 720. Referring to FIG. 7B, the ferrule 710 may be compressed such that the ferrule 710 expands to form an interference fit with the hole 730 formed in the substrate 720 and becomes flush with a first surface 722 and/or a second surface 724 of the substrate 720. In an alternative embodiment, the length $L_2$ of the ferrule 710 may be approximately the same as the thickness $t_4$ of the substrate and the OD $d_4$ of the ferrule 710 may be approximately the same as the diameter $d_5$ of the hole 730 formed in the substrate 720. The hole 730 formed in the substrate 720 may be match drilled to the OD $d_4$ of the ferrule 710 to provide a specified annular space between the OD $d_4$ of the ferrule and the hole 730. The annular space may be filled with adhesive and cured to form a bond between the ferrule 710 and the substrate 720.

Figure 7C:
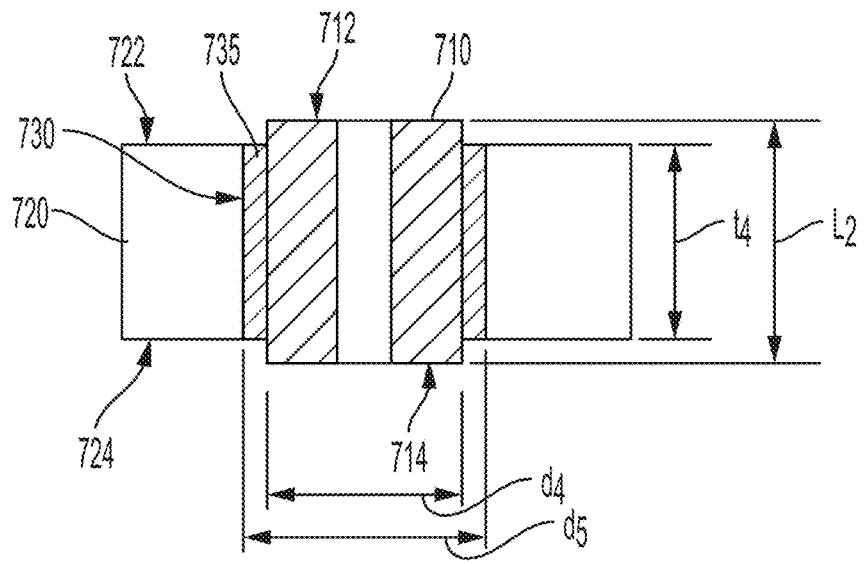
FIG. 7C is a cross-sectional view illustrating another embodiment of a via formed with a ferrule without a flange in accordance with various aspects of the present disclosure.

FIG. 7C is a cross-sectional view illustrating another embodiment of a via formed with a ferrule without a flange in accordance with various aspects of the present disclosure. Referring to FIG. 7C, a ferrule 710 may have a length $L_2$ greater than a thickness $t_4$ of a substrate 720 (e.g., a ceramic substrate or other substrate), and an outside diameter (OD) $d_4$ less than a diameter $d_5$ of a hole 730 formed in the substrate 720. The ferrule 710 may be positioned in the hole 730 in the substrate 720 with respect to the first surface 722 and/or the second surface 724 of the substrate 720 such that a first surface 712 of the ferrule 710 is disposed at a first position substantially flush with the first surface 722 of the substrate 720 or the second surface 714 of the ferrule 710 is disposed at a position substantially flush with the second surface 724 of the substrate 720 or the ferrule 710 may be disposed at any position between the first and second positions. After the ferrule 710 is inserted into the hole 730 in the substrate 720, the remaining annular space between the ferrule 710 and the hole 730 in the substrate 720 may be filled with an adhesive 735 (i.e., a platinum-gold (Pt—Au) ink, a ceramic-platinum-gold (ceramic-Pt—Au) ink, or another adhesive). The adhesive may be cured, for example by firing, to form a bond between the substrate 720 and the ferrule 710.

Figure 8:
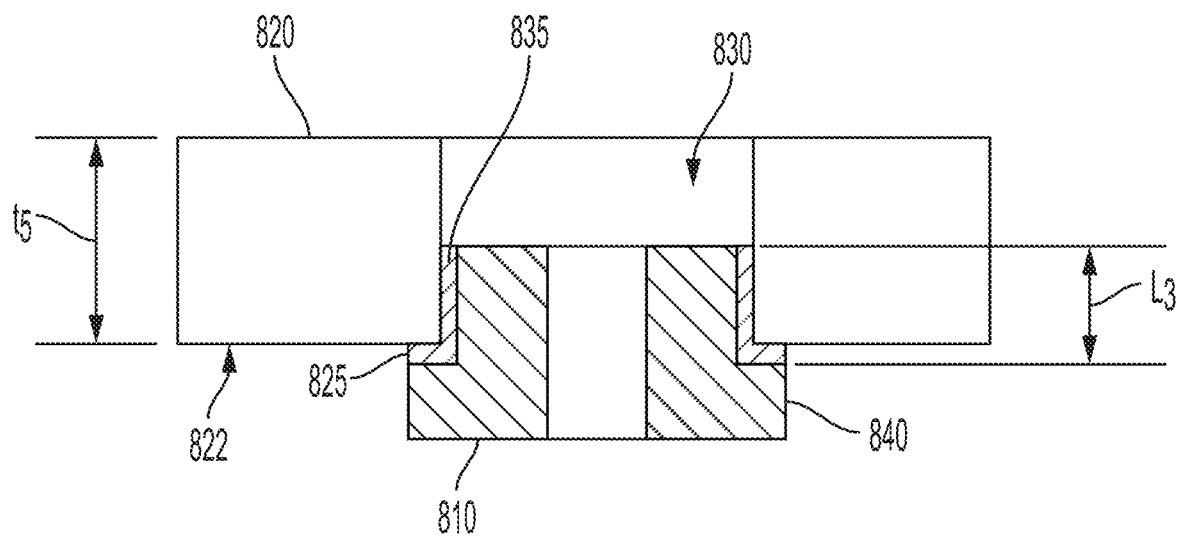
FIG. 8 is a cross-sectional view illustrating a flanged ferrule having a main body length less than the thickness of a substrate in accordance with various aspects of the present disclosure.

In another alternate embodiment, a ferrule may have a length less than the thickness of a substrate into which it is inserted. FIG. 8 is a cross-sectional view illustrating a flanged ferrule having a main body length less than the thickness of a substrate in accordance with various aspects of the present disclosure. Referring to FIG. 8, the ferrule 810 may have a main body length $L_3$ less than the thickness $t_5$ of the substrate 820 (i.e., a ceramic substrate or other substrate). For example, the length $L_3$ may be approximately one half or another fraction of the thickness $t_5$ of the substrate 820. A hole 830 in the substrate 820 may be match drilled to the OD of the of the main body of the ferrules 810 to provide a specified annular space between the OD of the main body of the ferrule and the hole 830.

A first adhesive 825 (i.e., a platinum-gold (Pt—Au) ink, a ceramic-platinum-gold (ceramic-Pt—Au) ink, or another adhesive) may be applied to a first surface 822 of the substrate 820 around a circumference of each of the hole 830 prior to insertion of the ferrule 310 into the hole. The first adhesive 825 may adhere the flange 840 of the ferrule 810 to the substrate 820. After the ferrule 810 is inserted into the hole 830 in the substrate 820, the remaining annular space between the ferrule 810 and the hole 830 in the substrate 820 may be filled with a second adhesive 835 (i.e., a platinum-gold (Pt—Au) ink, a ceramic-platinum-gold (ceramic-Pt—Au) ink, or another adhesive). The first adhesive and the second adhesive may be cured, for example by firing, to form a bond between the substrate 820 and the ferrule 810.

Figure 9:
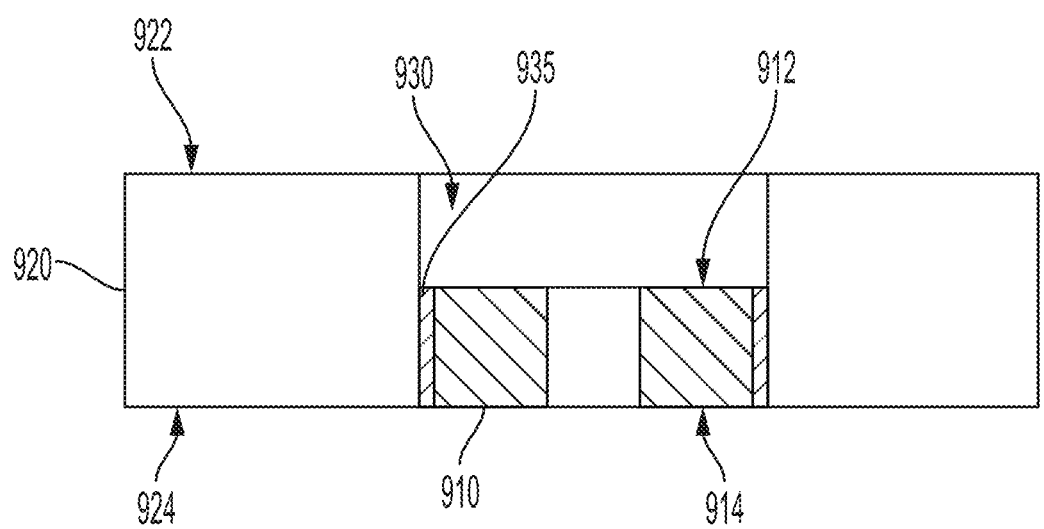
FIG. 9 is a cross-sectional view illustrating a ferrule without a flange having a main body length less than the thickness of a substrate in accordance with various aspects of the present disclosure.

FIG. 9 is a cross-sectional view illustrating a ferrule without a flange having a main body length less than the thickness of a substrate in accordance with various aspects of the present disclosure. Referring to FIG. 9, the ferrule 910 may have a main body length $L_4$ less than the thickness $t_6$ of the substrate 920 (i.e., a ceramic substrate or other substrate). For example, the length $L_4$ may be approximately one half or another fraction of the thickness $t_6$ of the substrate 920. A hole 930 in the substrate 920 may be match drilled to the OD of the of the main body of the ferrules 910 to provide a specified annular space between the OD of the main body of the ferrule and the hole 930.

The ferrule 910 may be positioned in the hole 930 in the substrate 920 with respect to the first surface 922 and/or the second surface 924 of the substrate 920 such that a first surface 912 of the ferrule 910 is disposed at a first position substantially flush with the first surface 922 of the substrate 920 or the second surface 914 of the ferrule 910 is disposed at a position substantially flush with the second surface 924 of the substrate 920 or the ferrule 910 may be disposed at any position between the first and second positions. After the ferrule 910 is inserted into the hole 930 in the substrate 920, the remaining annular space between the ferrule 910 and the hole 930 in the substrate 920 may be filled with an adhesive 935 (i.e., a platinum-gold (Pt—Au) ink, a ceramic-platinum-gold (ceramic-Pt—Au) ink, or another adhesive). The adhesive may be cured, for example by firing, to form a bond between the substrate 920 and the ferrule 910.

Figure 10:
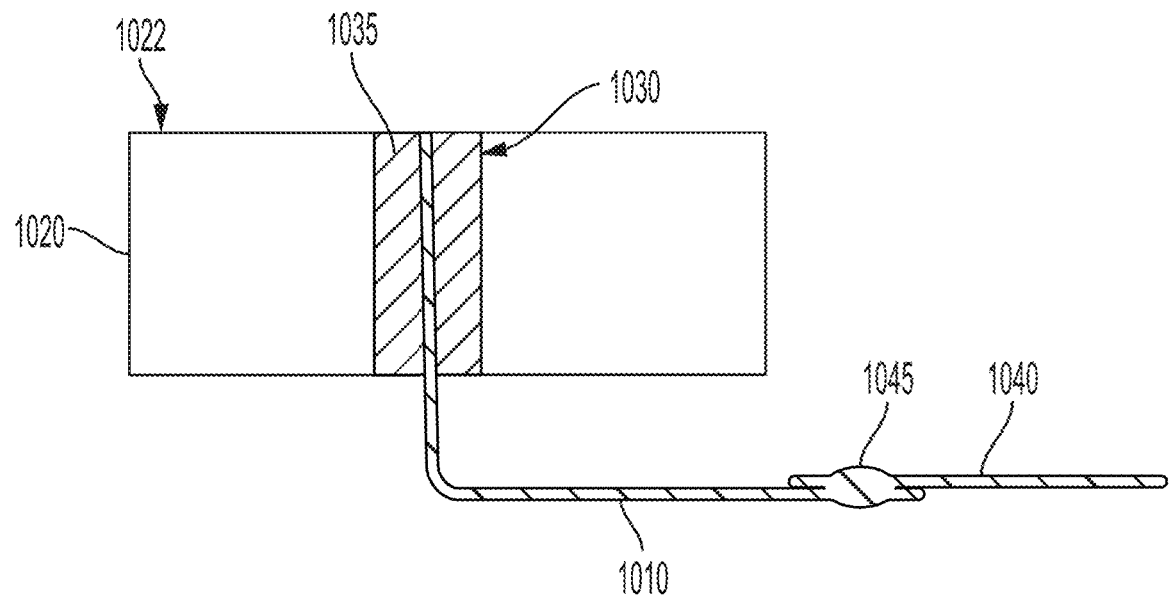
FIG. 10 is a cross-sectional view of via configured for lead to lead connection in accordance with various aspects of the present disclosure.

FIG. 10 is a cross-sectional view of via configured for lead to lead connection in accordance with various aspects of the present disclosure. Referring to FIG. 10, the substrate 1020 may have a hole 1030 (i.e., a via) having a diameter larger than the diameter of a wire lead 1010. The wire lead 1010 may be, for example, a Pt—Ir wire lead or a metal lead having another composition. The hole 1030 in the substrate 1020 may be filled with an adhesive 1035, for example, a platinum-gold (Pt—Au) ink, a ceramic-platinum-gold (ceramic-Pt—Au) ink, or another adhesive. The wire lead 1010 may be inserted into the adhesive 1035 until the wire lead 1010 is substantially flush with a first surface 1022 of the substrate 1020, and the adhesive 1035 may be cured. The adhesive may be cured, for example by firing, to form a bond between the substrate 1020 and the wire lead 1010. The cured adhesive 1035 may provide a mechanical and electrical connection for the wire lead 1010. The wire lead 1010 may be connected to a second wire lead 1040 from an electronics package (not shown) by a weld joint 1045. The weld joint 1045 may be formed by, for example, laser welding or other suitable welding technology.

Figure 11:
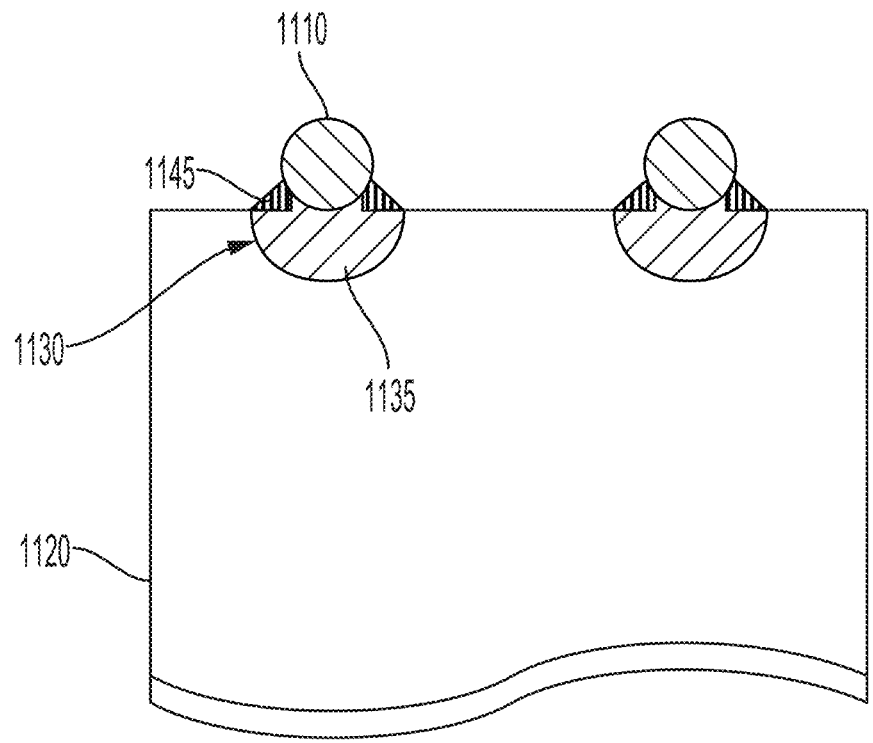
FIG. 11 is a top view of a wire lead connection to a substrate in accordance with various aspects of the present disclosure.

FIG. 11 is a top view of a wire lead connection to a substrate in accordance with various aspects of the present disclosure. Referring to FIG. 11, the substrate 1120 may have a plurality of drilled holes 1130. After the holes 1130 are drilled in the substrate 1120, the substrate 1120 may be cut approximately through the centerline of the holes 1130 exposing the remaining portions of the holes 1130 at an edge of the substrate 1120. Alternatively, semicircular notches may be formed at the edge of the substrate 1120, for example by drilling the semicircular notches or by another process. The remaining portions of the holes 1130 at an edge of the substrate 1120 may be filled with an adhesive 1035, for example, a platinum-gold (Pt—Au) ink, a ceramic-platinum-gold (ceramic-Pt—Au) ink, or another adhesive, and the substrate 1120 and adhesive 1135 fired to cure the adhesive 1135. Lead wires 1110, for example, a Pt—Ir wire lead or a metal lead having another composition, may be connected to the exposed cured adhesive 1035 at the edge of the substrate 1120 by forming welds 1145 between the lead wires 1110 and the exposed cured adhesive 1035. The welds 1145 may be formed by, for example, laser welding or other suitable welding technology. In some embodiments, the portions of the lead wires 1110 forming the welds 1145 may be flattened prior to welding.

Figure 12:
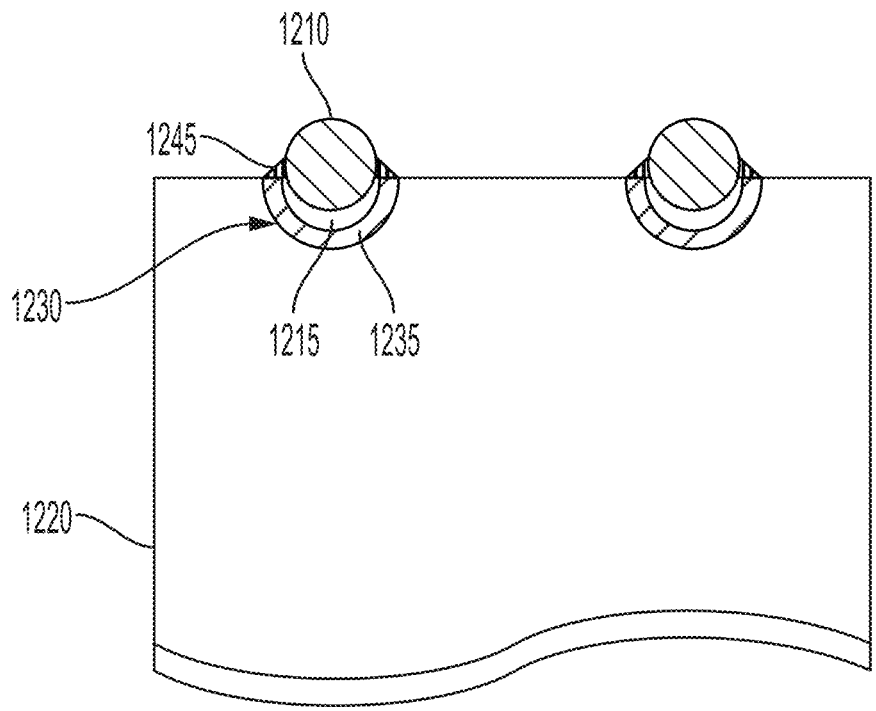
FIG. 12 is a top view of another embodiment of a wire lead connection to a substrate in accordance with various aspects of the present disclosure.

FIG. 12 is a top view of another embodiment of a wire lead connection to a substrate in accordance with various aspects of the present disclosure. Referring to FIG. 12, the substrate 1220 may have a plurality of drilled holes 1230. A ferrules 1215 having an OD smaller than a diameter of the holes 1230 may be placed in each of the holes 1230. The remaining annular space between the OD of the ferrules 1215 and the diameter of the holes 1230 in the substrate 1220 may be filled with an adhesive 1235, for example, a platinum-gold (Pt—Au) ink, a ceramic-platinum-gold (ceramic-Pt—Au) ink, or another adhesive, and the substrate 1220, the ferrules 1215, and the adhesive 1235 fired to cure the adhesive 1235. After the adhesive 1235 is cured, the substrate 1220 may be cut approximately through the centerline of the holes 1230 exposing the remaining portions of the holes 1230 and half-ferrules 1215 at an edge of the substrate 1220. Alternatively, semicircular notches may be formed at the edge of the substrate 1220, for example by drilling the semicircular notches or by another process and half-ferrules may be placed in the semicircular notches and bonded to the substrate 1220 with an adhesive 1235 as described above. Lead wires 1210, for example, a Pt—Ir wire lead or a metal lead having another composition, may be connected to the exposed half-ferrules 1215 at the edge of the substrate 1120 by forming welds 1245 between the lead wires 1210 and the exposed half-ferrules 1215. The welds 1245 may be formed by, for example, laser welding or other suitable welding technology.

Figure 13:
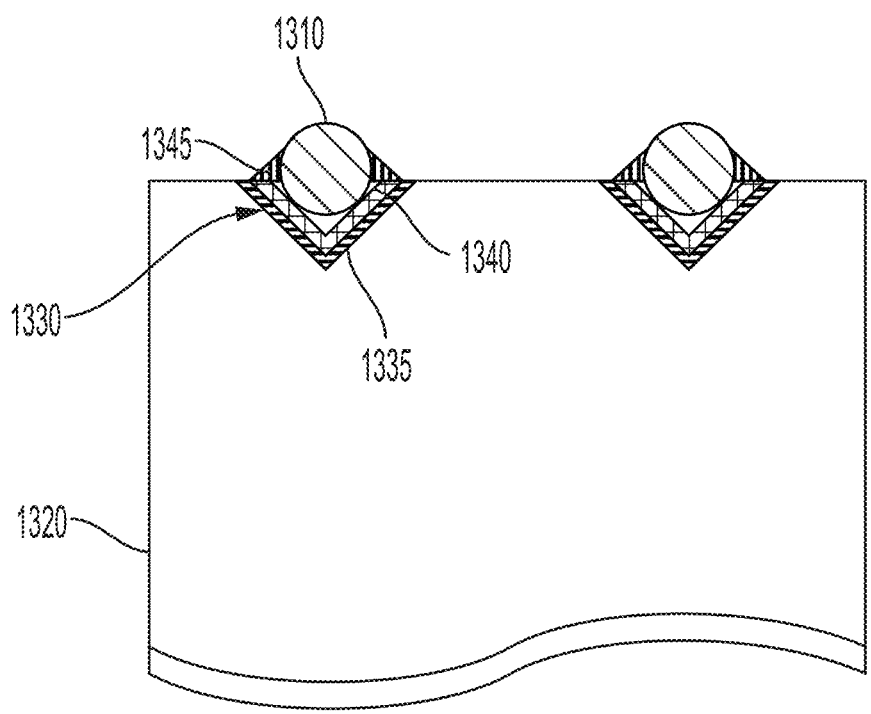
FIG. 13 is a top view of another embodiment of a wire lead connection to a substrate in accordance with various aspects of the present disclosure.

FIG. 13 is a top view of another embodiment of a wire lead connection to a substrate in accordance with various aspects of the present disclosure. Referring to FIG. 13, the substrate 1320 may have a plurality notches 1330. An adhesive 1335, for example, a platinum-gold (Pt—Au) ink, a ceramic-platinum-gold (ceramic-Pt—Au) ink, or another adhesive, may be coated on surfaces of the notches. An interposing material 1340, for example, a Pt—Ir foil or a metal foil having another composition, may be placed over the adhesive 1335 and the substrate 1320, the interposing material 1340, and the adhesive 1335 fired to cure the adhesive 1335 and bond the interposing material 1340 to the substrate 1320. Lead wires 1310, for example, a Pt—Ir wire lead or a metal lead having another composition, may be connected to the interposing material 1340 in the notches 1330 in the substrate 1320 by forming welds 1345 between the lead wires 1310 and the interposing material 1340. The welds 1345 may be formed by, for example, laser welding or other suitable welding technology.

Figure 14:
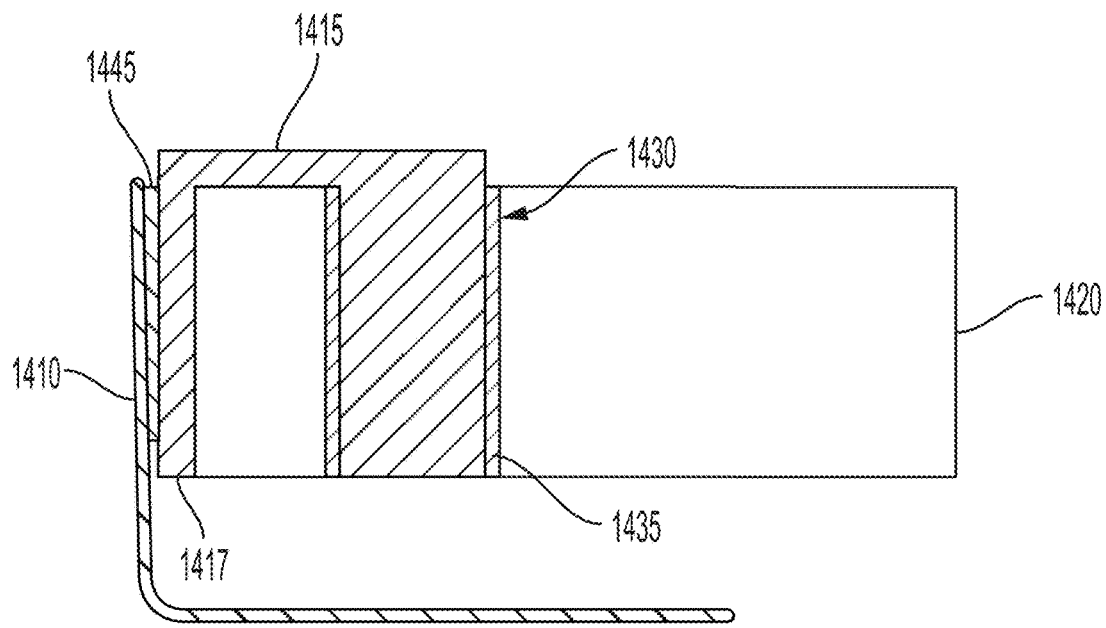
FIG. 14 is a cross-sectional view of another embodiment of a wire lead connection to a substrate in accordance with various aspects of the present disclosure.

FIG. 14 is a cross-sectional view of another embodiment of a wire lead connection to a substrate in accordance with various aspects of the present disclosure. Referring to FIG. 14, the substrate 1420 may have a plurality of drilled holes 1430. A contact 1415 having an OD smaller than a diameter of the holes 1430 may be placed in each of the holes 1430 may be inserted into each of the holes 1430. The contact 1415 may have an extended portion 1417 that extends over an end of the substrate 1420. After the contact 1415 is placed in the hole 1430, the remaining annular space between the OD of the contact 1415 and the diameter of the hole 1430 in the substrate 1420 may be filled with an adhesive 1435, for example, a platinum-gold (Pt—Au) ink, a ceramic-platinum-gold (ceramic-Pt—Au) ink, or another adhesive. The substrate 1420, the contacts 1415, and the adhesive 1435 may be fired to cure the adhesive 1435. After the adhesive 1435 is cured, lead wires 1410, for example, a Pt—Ir wire lead or a metal lead having another composition, may be connected to the extended portion 1417 of the contact 1415 at the edge of the substrate 1420 by forming a weld 1445 between the lead wires 1410 and the extended portion 1417 of the contact 1415. The weld 1445 may be formed by, for example, laser welding or other suitable welding technology. In some embodiments, the extended portion 1417 of the contact 1415 may include a geometrical feature, for example, a notch or groove or other geometrical feature configured to accommodate the lead wires 1410 and facilitate welding of the lead wires 1410 to the extended portion 1417 of the contact 1415.

Figure 15:
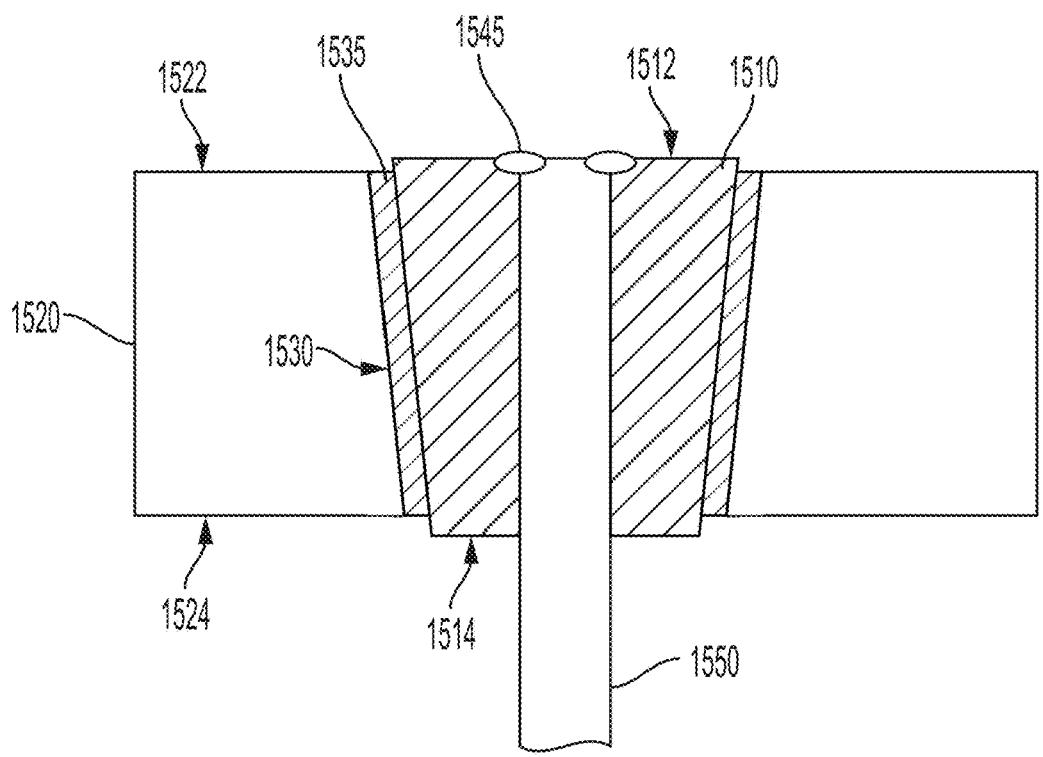
FIG. 15 is a cross-sectional view illustrating another embodiment of a via formed with a ferrule in accordance with various aspects of the present disclosure.

FIG. 15 is a cross-sectional view illustrating another embodiment of a via formed with a ferrule in accordance with various aspects of the present disclosure. Referring to FIG. 15, a tapered hole 1530 may be formed in the substrate 1520. The tapered hole 1530 may be coated with an adhesive 1535, for example, a platinum-gold (Pt—Au) ink, a ceramic-platinum-gold (ceramic-Pt—Au) ink, or another adhesive. A tapered ferrule 1510 having a taper matching the tapered hole 1530 may be inserted into the tapered hole 1530 and the substrate 1520, tapered ferrule 1510, and the adhesive 1535 may be fired to cure the adhesive 1535 and bond the tapered ferrule 1510 to the substrate 1520. The tapered ferrule 1510 may protrude from a first surface 1522 or a second surface 1524 the substrate 1520 or from both the first and second surfaces 1522, 1524 of the substrate 1520. Alternatively, the tapered ferrule 1510 may be substantially flush with both the first and second surfaces 1522, 1524 of the substrate.

The end of a wire lead 1550 inserted into the through hole 1530 of the ferrule 1510 from a second surface 1514 of the ferrule 1510 and may be positioned approximately even with a first surface 1512 of the ferrule 1510. A weld joint 1545 may be formed around a circumference of the through hole 1530 between the end of the wire lead 1550 inserted into the ferrule 1510 and the first surface 1512 of the ferrule 1510. The weld joint 1545 may be formed by laser welding or another suitable welding technology. Alternatively, the end of the wire lead 1550 may be inserted into the through hole 1530 of the ferrule 1510 from the first surface 1512 of the ferrule 1510 and may be positioned approximately even with the second surface 1514 of the ferrule 1510 and the weld joint formed around a circumference of the through hole 1530 between the end of the wire lead 1550 inserted into the ferrule 1510 and the second surface 1514 of the ferrule 1510.

Embodiments of the present disclosure provide solutions that enable including PCB antennas as well as other electronic assemblies in a biomedical implant without the need to place them in a hermetic enclosure. The provided solutions may also be implemented for other ceramic-substrate based electronics that are being joined via laser welding or other welding technologies and have similar deployment and processing limitations. The disclosed embodiments may streamline manufacturing processes, enable improved visual inspection of the weld, and maintain high electrical conductivity of the overall joint without adversely affecting electrical performance.

The examples and embodiments described herein are for illustrative purposes only. Various modifications or changes in light thereof will be apparent to persons skilled in the art. These are to be included within the spirit and purview of this application, and the scope of the appended claims, which follow.

What is claimed is:

1. A biocompatible electrical connector, comprising:
a substrate comprising a ceramic material;
a ferrule comprising a concentric flange at a first end of the ferrule;
a first adhesive; and
a second adhesive,
wherein:
the first adhesive adheres a first surface of the concentric flange of the ferrule to a surface of the substrate,
the second adhesive fills an annular space between a hole in the substrate and the ferrule, and
the first adhesive or the second adhesive forms a conductive path on the surface of the substrate between the ferrule and a circuit pattern formed directly on the substrate.

2. The biocompatible electrical connector of claim 1, wherein the first adhesive and the second adhesive comprise one of a platinum-gold ink or a gold ink or a combination thereof.

3. The biocompatible electrical connector of claim 1, wherein the conductive path is screen-printed on the surface of the substrate.

4. The biocompatible electrical connector of claim 1, wherein the ferrule comprises one of a platinum-iridium (Pt—Ir) material or an implant grade stainless steel.

5. A method for forming a biocompatible electrical connection, the method comprising:
applying a first adhesive on a surface of a substrate around a circumference of a hole in the substrate, wherein the substrate comprises a ceramic material;
inserting a ferrule comprising a concentric flange at a first end into the hole, wherein the first adhesive adheres a first surface of the concentric flange to the surface of the substrate;
filling an annular space between the hole and the ferrule with a second adhesive; and
forming a conductive path between the ferrule and a circuit pattern formed directly on the surface of the substrate using the first adhesive or the second adhesive.

6. The method of claim 5, wherein the first adhesive and the second adhesive comprise one of a platinum-gold ink or a gold ink or a combination thereof.

7. The method of claim 5, further comprising screen-printing the conductive path on the surface of the substrate.

8. The method of claim 5, wherein the ferrule comprises one of a platinum-iridium (Pt—Ir) material or an implant grade stainless steel.

9. A biocompatible device, comprising:
electronic circuitry enclosed in a conductive biocompatible housing;
a biocompatible antenna disposed external to the conductive biocompatible housing and electrically connected to the electronic circuitry; and
a biocompatible electrical connector configured to electrically connect the biocompatible antenna to the electronic circuitry,
wherein the biocompatible electrical connector comprises:
a ferrule having a concentric flange at a first end of the ferrule;
a first adhesive;
a second adhesive; and
a substrate comprising a ceramic material,
wherein the first adhesive adheres a first surface of the concentric flange of the ferrule to a surface of the substrate,
wherein the second adhesive fills an annular space between a hole in the substrate and the ferrule, and
the first adhesive or the second adhesive forms a conductive path on the surface of the substrate between the ferrule and a circuit pattern formed directly on the substrate.

10. The biocompatible device of claim 9, wherein the first adhesive and the second adhesive comprise one of a platinum-gold ink or a gold ink or a combination thereof.

11. The biocompatible device of claim 9, wherein the conductive path is screen-printed on the surface of the substrate.

12. The biocompatible device of claim 9, wherein the ferrule comprises one of a platinum-iridium (Pt—Ir) material or an implant grade stainless steel.

* * * * *